(12) United States Patent
Huebner (10) Patent No.: US 7,537,604 B2
(45) Date of Patent: May 26, 2009

(54) BONE PLATES WITH SLOTS

(75) Inventor: Randall J. Huebner, Beaverton, OR (US)

(73) Assignee: Acumed LLC, Hillsboro, OR (US)

( * ) Notice: Subject to any disclaimer, the term of this patent is extended or adjusted under 35 U.S.C. 154(b) by 597 days.

(21) Appl. No.: 10/717,015

(22) Filed: Nov. 19, 2003

(65) Prior Publication Data
US 2004/0102775 A1     May 27, 2004

Related U.S. Application Data

(60) Provisional application No. 60/512,323, filed on Oct. 17, 2003.

(51) Int. Cl.
*A61B 17/88* (2006.01)
(52) U.S. Cl. ...................................... 606/281
(58) Field of Classification Search ............. 606/69–73, 606/60, 61
See application file for complete search history.

(56) References Cited

U.S. PATENT DOCUMENTS

| | | |
|---|---|---|
| 820,503 A | 5/1906 | Krengel et al. |
| 869,697 A | 10/1907 | Eilhauer et al. |
| 1,105,105 A | 7/1914 | Sherman |
| 1,345,425 A | 7/1920 | Wells |
| 1,789,060 A | 1/1931 | Weisenbach |
| 1,889,239 A | 11/1932 | Crowley |
| 2,406,832 A | 9/1946 | Hardinge |
| 2,443,363 A | 6/1948 | Townsend et al. |
| 2,489,870 A | 11/1949 | Dzus |
| 2,494,229 A | 1/1950 | Collison |
| 2,500,370 A | 3/1950 | McKibbin |
| 2,526,959 A | 10/1950 | Lorenzo |
| 2,580,821 A | 1/1952 | Nicola |
| 2,583,896 A | 1/1952 | Siebrandt |
| 2,737,835 A | 3/1956 | Herz |
| 3,025,853 A | 3/1962 | Mason |
| 3,072,423 A | 1/1963 | Charlton |
| 3,171,518 A | 3/1965 | Bergmann |
| 3,244,170 A | 4/1966 | McElvenny |
| 3,346,894 A | 10/1967 | Lemelson |
| 3,386,437 A | 6/1968 | Treace |
| 3,488,779 A | 1/1970 | Christensen |
| 3,489,143 A | 1/1970 | Halloran |
| 3,593,709 A | 7/1971 | Halloran |
| 3,604,414 A | 9/1971 | Borges |
| 3,716,050 A | 2/1973 | Johnston |
| 3,741,205 A | 6/1973 | Markolf et al. |

(Continued)

FOREIGN PATENT DOCUMENTS

AU         89750/91         2/1992

(Continued)

OTHER PUBLICATIONS

McBride S.M.O. Stainless Steel Bone Plates brochure, DePuy, Inc., 1943.

(Continued)

*Primary Examiner*—Anu Ramana
(74) *Attorney, Agent, or Firm*—Kolisch Hartwell, PC (57) ABSTRACT

Bone plates having slots configured to permit positioning of the bone plates on bone, and methods of using the bone plates for bone fixation.

22 Claims, 4 Drawing Sheets

U.S. PATENT DOCUMENTS

| | | | |
|---|---|---|---|
| 3,779,240 A * | 12/1973 | Kondo .................. 606/69 |
| 3,842,825 A | 10/1974 | Wagner |
| 3,866,458 A | 2/1975 | Wagner |
| 3,900,025 A | 8/1975 | Barnes, Jr. |
| 3,901,064 A | 8/1975 | Jacobson |
| 3,939,497 A | 2/1976 | Heimke et al. |
| 3,965,720 A | 6/1976 | Goodwin et al. |
| 4,119,092 A | 10/1978 | Gil |
| 4,187,840 A | 2/1980 | Watanabe |
| 4,187,841 A | 2/1980 | Knutson |
| 4,201,215 A | 5/1980 | Crossett et al. |
| 4,364,382 A | 12/1982 | Mennen |
| 4,388,921 A | 6/1983 | Sutter et al. |
| 4,408,601 A | 10/1983 | Wenk |
| RE31,628 E | 7/1984 | Allgower et al. |
| 4,457,307 A | 7/1984 | Stillwell |
| 4,484,570 A | 11/1984 | Sutter et al. |
| 4,493,317 A | 1/1985 | Klaue |
| 4,506,681 A | 3/1985 | Mundell |
| 4,513,744 A | 4/1985 | Klaue |
| 4,565,192 A | 1/1986 | Shapiro |
| 4,565,193 A * | 1/1986 | Streli .................. 606/69 |
| 4,573,458 A | 3/1986 | Lower |
| 4,651,724 A | 3/1987 | Berentey et al. |
| 4,683,878 A | 8/1987 | Carter |
| 4,703,751 A | 11/1987 | Pohl |
| 4,718,413 A | 1/1988 | Johnson |
| 4,730,608 A | 3/1988 | Schlein |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,776,330 A * | 10/1988 | Chapman et al. .............. 606/64 |
| 4,794,918 A | 1/1989 | Wolter |
| 4,800,874 A | 1/1989 | David et al. |
| 4,823,780 A | 4/1989 | Odensten et al. |
| 4,867,144 A | 9/1989 | Karas et al. |
| 4,892,093 A | 1/1990 | Zarnowski et al. |
| 4,893,619 A | 1/1990 | Dale et al. |
| 4,903,691 A | 2/1990 | Heinl |
| 4,905,679 A | 3/1990 | Morgan |
| 4,923,471 A | 5/1990 | Morgan |
| 4,926,847 A | 5/1990 | Luckman |
| 4,943,292 A | 7/1990 | Foux |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karas et al. |
| 4,966,599 A | 10/1990 | Pollock |
| 4,973,332 A | 11/1990 | Kummer |
| 4,988,350 A * | 1/1991 | Herzberg .................. 606/65 |
| 5,002,544 A | 3/1991 | Klaue et al. |
| 5,006,120 A | 4/1991 | Carter |
| 5,013,315 A | 5/1991 | Barrows |
| 5,015,248 A | 5/1991 | Burstein et al. |
| 5,021,056 A | 6/1991 | Hofmann et al. |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,129,899 A | 7/1992 | Small et al. |
| 5,133,718 A | 7/1992 | Mao |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |
| 5,190,544 A | 3/1993 | Chapman et al. |
| 5,190,545 A | 3/1993 | Corsi et al. |
| 5,197,966 A | 3/1993 | Sommerkamp |
| 5,201,737 A | 4/1993 | Leibinger et al. |
| 5,234,431 A | 8/1993 | Keller |
| 5,254,119 A | 10/1993 | Schreiber |
| 5,269,784 A | 12/1993 | Mast |
| 5,290,288 A | 3/1994 | Vignaud et al. |
| 5,304,180 A | 4/1994 | Slocum |
| 5,314,490 A | 5/1994 | Wagner et al. |
| 5,364,398 A * | 11/1994 | Chapman et al. .............. 606/69 |
| 5,364,399 A | 11/1994 | Lowery et al. |
| 5,380,327 A | 1/1995 | Eggers et al. |
| 5,413,577 A | 5/1995 | Pollock |
| 5,413,579 A | 5/1995 | Du Toit |
| 5,423,826 A | 6/1995 | Coates et al. |
| 5,443,516 A | 8/1995 | Albrektsson et al. |
| 5,468,242 A | 11/1995 | Reisberg |
| 5,474,553 A | 12/1995 | Baumgart |
| 5,487,741 A | 1/1996 | Maruyama et al. |
| 5,487,743 A | 1/1996 | Laurain et al. |
| 5,522,902 A | 6/1996 | Yuan et al. |
| 5,527,311 A | 6/1996 | Procter et al. |
| 5,531,745 A | 7/1996 | Ray |
| 5,534,027 A | 7/1996 | Hodorek |
| 5,545,228 A | 8/1996 | Kambin |
| 5,564,302 A | 10/1996 | Watrous |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,607,426 A | 3/1997 | Ralph et al. |
| 5,643,261 A | 7/1997 | Schafer et al. |
| 5,643,265 A | 7/1997 | Errico et al. |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,667 A | 10/1997 | Hausman |
| 5,681,311 A * | 10/1997 | Foley et al. .................. 606/61 |
| 5,681,313 A | 10/1997 | Diez |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,728,127 A * | 3/1998 | Asher et al. .................. 606/61 |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,807,396 A | 9/1998 | Raveh |
| 5,810,823 A | 9/1998 | Klaue et al. |
| 5,810,824 A | 9/1998 | Chan |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |
| 5,902,304 A | 5/1999 | Walker et al. |
| 5,904,683 A | 5/1999 | Pohndorf et al. |

| | | | | | | |
|---|---|---|---|---|---|---|
| 5,916,216 | A | 6/1999 | DeSatnick et al. | 6,440,135 B2 | 8/2002 | Orbay et al. |
| 5,919,195 | A | 7/1999 | Wilson et al. | 6,454,769 B2 | 9/2002 | Wagner et al. |
| 5,928,234 | A | 7/1999 | Manspeizer | 6,454,770 B1 | 9/2002 | Klaue |
| 5,931,839 | A | 8/1999 | Medoff | 6,458,133 B1 | 10/2002 | Lin |
| 5,938,664 | A | 8/1999 | Winquist et al. | 6,503,250 B2 | 1/2003 | Paul |
| 5,941,878 | A | 8/1999 | Medoff | 6,508,819 B1 | 1/2003 | Orbay |
| 5,951,557 | A | 9/1999 | Luter | 6,514,274 B1 | 2/2003 | Boucher et al. |
| 5,954,722 | A | 9/1999 | Bono | 6,520,965 B2 | 2/2003 | Chervitz et al. |
| 5,964,763 | A | 10/1999 | Incavo et al. | 6,527,775 B1 | 3/2003 | Warburton |
| 5,968,046 | A | 10/1999 | Castleman | 6,533,789 B1 | 3/2003 | Hall, IV et al. |
| 5,968,047 | A | 10/1999 | Reed | 6,547,790 B2 | 4/2003 | Harkey et al. |
| 5,973,223 | A | 10/1999 | Tellman et al. | 6,565,570 B2 | 5/2003 | Sterett et al. |
| 6,001,099 | A | 12/1999 | Huebner | 6,592,578 B2 | 7/2003 | Henniges et al. |
| 6,004,323 | A | 12/1999 | Park et al. | 6,595,993 B2 | 7/2003 | Donno et al. |
| 6,004,353 | A | 12/1999 | Masini | 6,602,255 B1 | 8/2003 | Campbell et al. |
| 6,007,535 | A | 12/1999 | Rayhack et al. | 6,623,486 B1 | 9/2003 | Weaver et al. |
| 6,022,350 | A | 2/2000 | Ganem | 6,623,487 B1 | 9/2003 | Goshert |
| 6,027,504 | A | 2/2000 | McGuire | 6,682,531 B2 | 1/2004 | Winquist et al. |
| 6,053,915 | A | 4/2000 | Bruchmann | 6,682,533 B1 | 1/2004 | Dinsdale et al. |
| 6,077,266 | A | 6/2000 | Medoff | 6,689,139 B2 | 2/2004 | Horn |
| 6,077,271 | A | 6/2000 | Huebner et al. | 6,695,846 B2 | 2/2004 | Richelsoph et al. |
| 6,093,188 | A | 7/2000 | Murray | 6,706,046 B2 | 3/2004 | Orbay et al. |
| 6,096,040 | A | 8/2000 | Esser | 6,712,820 B2 | 3/2004 | Orbay |
| 6,113,603 | A | 9/2000 | Medoff | 6,719,759 B2 | 4/2004 | Wagner et al. |
| 6,117,160 | A | 9/2000 | Bonutti | 6,730,090 B2 | 5/2004 | Orbay et al. |
| 6,123,709 | A | 9/2000 | Jones | 6,730,091 B1 | 5/2004 | Pfefferle et al. |
| 6,129,728 | A | 10/2000 | Schumacher et al. | 6,736,819 B2 | 5/2004 | Tipirneni |
| 6,129,730 | A | 10/2000 | Bono et al. | 6,767,351 B2 | 7/2004 | Orbay et al. |
| 6,139,548 | A | 10/2000 | Errico | 6,793,658 B2 | 9/2004 | LeHuec et al. |
| 6,152,927 | A | 11/2000 | Farris et al. | 6,821,278 B2 | 11/2004 | Frigg et al. |
| 6,159,213 | A | 12/2000 | Rogozinski | 6,858,031 B2 | 2/2005 | Morrison et al. |
| 6,179,839 | B1 | 1/2001 | Weiss et al. | 6,866,665 B2 | 3/2005 | Orbay |
| 6,183,475 | B1 | 2/2001 | Lester et al. | 6,893,444 B2 | 5/2005 | Orbay |
| 6,193,721 | B1 | 2/2001 | Michelson | 6,955,677 B2 | 10/2005 | Dahners |
| 6,197,028 | B1 | 3/2001 | Ray et al. | 7,044,952 B2 * | 5/2006 | Michelson .................. 606/71 |
| 6,221,073 | B1 | 4/2001 | Weiss et al. | 7,090,676 B2 * | 8/2006 | Huebner et al. ............. 606/71 |
| 6,224,602 | B1 | 5/2001 | Hayes | 2001/0011172 A1 | 8/2001 | Orbay et al. |
| 6,228,087 | B1 | 5/2001 | Fenaroli et al. | 2002/0004660 A1 | 1/2002 | Henniges et al. |
| 6,235,033 | B1 | 5/2001 | Brace et al. | 2002/0032446 A1 | 3/2002 | Orbay |
| 6,235,034 | B1 | 5/2001 | Bray | 2002/0055741 A1 | 5/2002 | Schlapfer et al. |
| 6,238,396 | B1 | 5/2001 | Lombardo | 2002/0128654 A1 | 9/2002 | Steger et al. |
| 6,258,092 | B1 | 7/2001 | Dall | 2002/0143336 A1 | 10/2002 | Hearn |
| 6,261,291 | B1 | 7/2001 | Talaber et al. | 2002/0143338 A1 | 10/2002 | Orbay et al. |
| 6,273,889 | B1 | 8/2001 | Richelsoph | 2002/0147453 A1 | 10/2002 | Gambale |
| 6,283,969 | B1 * | 9/2001 | Grusin et al. .................. 606/69 | 2002/0151899 A1 | 10/2002 | Bailey et al. |
| 6,290,703 | B1 | 9/2001 | Ganem | 2002/0156474 A1 | 10/2002 | Wack et al. |
| 6,302,883 | B1 | 10/2001 | Bono | 2002/0183752 A1 | 12/2002 | Steiner et al. |
| 6,302,884 | B1 | 10/2001 | Wellisz et al. | 2003/0040748 A1 | 2/2003 | Aikins et al. |
| 6,302,887 | B1 | 10/2001 | Spranza et al. | 2003/0055429 A1 | 3/2003 | Ip et al. |
| 6,306,136 | B1 | 10/2001 | Baccelli | 2003/0105461 A1 | 6/2003 | Putnam |
| 6,312,431 | B1 | 11/2001 | Asfora | 2003/0149434 A1 | 8/2003 | Paul |
| 6,315,779 | B1 | 11/2001 | Morrison et al. | 2003/0153918 A1 | 8/2003 | Putnam et al. |
| 6,322,562 | B1 | 11/2001 | Wolter | 2003/0233093 A1 | 12/2003 | Moles et al. |
| 6,325,803 | B1 | 12/2001 | Schumacher et al. | 2004/0102776 A1 | 5/2004 | Huebner |
| 6,331,179 | B1 | 12/2001 | Freid et al. | 2004/0102777 A1 | 5/2004 | Huebner |
| 6,336,927 | B2 | 1/2002 | Rogozinski | 2004/0102778 A1 | 5/2004 | Huebner et al. |
| 6,338,734 | B1 | 1/2002 | Burke et al. | 2004/0116930 A1 | 6/2004 | O'Driscoll et al. |
| 6,340,362 | B1 * | 1/2002 | Pierer et al. .................. 606/71 | 2004/0127901 A1 | 7/2004 | Huebner et al. |
| 6,342,055 | B1 | 1/2002 | Eisermann et al. | 2004/0127903 A1 | 7/2004 | Schlapfer et al. |
| 6,342,075 | B1 | 1/2002 | MacArthur | 2004/0153073 A1 | 8/2004 | Orbay |
| 6,355,036 | B1 | 3/2002 | Nakajima | 2004/0193164 A1 | 9/2004 | Orbay |
| 6,355,042 | B2 | 3/2002 | Winquist | 2004/0193165 A1 | 9/2004 | Orbay |
| 6,358,250 | B1 | 3/2002 | Orbay | 2004/0220566 A1 | 11/2004 | Bray |
| 6,364,881 | B1 | 4/2002 | Apgar et al. | 2004/0260291 A1 | 12/2004 | Jensen |
| 6,364,882 | B1 | 4/2002 | Orbay | 2004/0260292 A1 | 12/2004 | Orbay et al. |
| 6,364,883 | B1 | 4/2002 | Santilli | 2004/0260293 A1 | 12/2004 | Orbay et al. |
| 6,379,354 | B1 | 4/2002 | Rogozinski | 2004/0260294 A1 | 12/2004 | Orbay et al. |
| 6,379,364 | B1 | 4/2002 | Brace et al. | 2004/0260295 A1 | 12/2004 | Orbay et al. |
| 6,383,186 | B1 * | 5/2002 | Michelson .................. 606/69 | 2005/0015089 A1 | 1/2005 | Young et al. |
| 6,402,756 | B1 | 6/2002 | Ralph et al. | 2005/0049593 A1 | 3/2005 | Duong et al. |
| 6,413,259 | B1 | 7/2002 | Lyons et al. | 2005/0065520 A1 | 3/2005 | Orbay |
| 6,428,542 | B1 | 8/2002 | Michelson | 2005/0065522 A1 | 3/2005 | Orbay |
| 6,436,103 | B1 | 8/2002 | Suddaby | 2005/0065523 A1 | 3/2005 | Orbay |

| | | | |
|---|---|---|---|
| 2005/0065524 A1 | 3/2005 | Orbay | |
| 2005/0065528 A1 | 3/2005 | Orbay | |
| 2005/0085818 A1 | 4/2005 | Huebner | |
| 2005/0085819 A1 | 4/2005 | Ellis et al. | |
| 2005/0131413 A1 | 6/2005 | O'Driscoll et al. | |
| 2005/0159747 A1 | 7/2005 | Orbay | |
| 2005/0165395 A1 | 7/2005 | Orbay et al. | |
| 2005/0165400 A1 | 7/2005 | Fernandez | |
| 2005/0171544 A1 | 8/2005 | Falkner | |
| 2005/0182405 A1 | 8/2005 | Orbay et al. | |
| 2005/0182406 A1 | 8/2005 | Orbay et al. | |
| 2005/0187551 A1 | 8/2005 | Orbay et al. | |
| 2005/0192578 A1 | 9/2005 | Horst | |
| 2005/0234458 A1 | 10/2005 | Huebner | |

FOREIGN PATENT DOCUMENTS

| | | |
|---|---|---|
| CH | 611 147 | 5/1979 |
| DE | 2515430 | 11/1975 |
| DE | 4201531 | 7/1993 |
| DE | 4343117 | 6/1995 |
| EP | 0 053 999 | 6/1982 |
| EP | 0 410 309 | 1/1991 |
| EP | 0415837 A2 | 3/1991 |
| EP | 0471418 A1 | 2/1992 |
| EP | 0362049 B1 | 5/1992 |
| EP | 1 250 892 A2 | 9/2003 |
| EP | 1 250 892 A3 | 9/2003 |
| FR | 742.618 | 3/1933 |
| FR | 2 254 298 | 7/1975 |
| FR | 2367479 | 5/1978 |
| FR | 2405705 | 5/1979 |
| FR | 2405706 | 5/1979 |
| FR | 2406429 | 5/1979 |
| FR | 2472373 | 7/1981 |
| FR | 2674118 | 9/1992 |
| GB | 2245498 | 1/1992 |
| SU | 610518 | 6/1978 |
| SU | 718097 | 2/1980 |
| SU | 862937 | 9/1981 |
| SU | 897233 | 1/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 A | 2/1992 |
| SU | 1734715 A1 | 5/1992 |
| WO | WO82/01645 | 5/1982 |
| WO | WO87/02572 | 5/1987 |
| WO | WO88/03781 | 6/1988 |
| WO | WO96/29948 | 10/1996 |
| WO | WO 97/47251 | 12/1997 |
| WO | WO01/21083 A1 | 3/2001 |
| WO | WO01/62136 | 8/2001 |
| WO | WO 03/105712 A2 | 12/2003 |

OTHER PUBLICATIONS

Bone Plates brochure, Vitallium, Mar. 1948.
Dupont Distal Humeral Plates brochure, Howmedica Inc., 1990.
The Arnett-TMP* Titanium Miniplating System brochure, Techmedica, Inc., 1989.
Techmedica Bioengineers Keep Tabs on Your Needs brochure, Techmedica, Inc., 1991.
*A Comparison of Unicortical and Bicortical End Screw Attachment of Fracture Fixation Plates*, Beaupre et al., *Journal of Orthopaedic Trauma*, vol. 6, No. 3, pp. 294-300, 1992.
Ace 4.5/5.0 mm Titanium Cannulated Screw and Reconstruction Plate System surgical technique brochure, Ace Medical Company, 1992.
Ace 4.5/5.0 mm Titanium Cannulated Screw and Reconstruction Plate System simplified fracture fixation brochure, Ace Medical Company, 1992.
Ace Titanium 3.5/4.0 mm Screw and Plate System with the Ace 3.5 mm Universal Ribbon CT/MRI compatible fixation brochure, Ace Medical Company, 1992.
*Treatment of Three- and Four-Part Fractures of the Proximal Humerus with a Modified Cloverleaf Plate*, Esser, *Journal of Orthopaedic Trauma*, vol. 8, No. 1, pp. 15-22, 1994.
Ace Symmetry Titanium Upper Extremity Plates surgical technique brochure, Ace Medical Company, 1996.
The Ace Symmetry Titanium Upper Extremity Plates new product release brochure, Ace Medical Company, 1996.
Small Titanium Plates overview page, Synthes, p. 2a-33, Mar. 1997.
Congruent Distal Radius Plate System description, Acumed, Inc., Mar. 4, 1998.
*Salvage of Tibial Pilon Fractures Using Fusion of the Ankle with a 90° Cannulated Blade Plate: A Preliminary Report*, Morgan et al., *Foot & Ankle International*. vol. 20, No. 6, pp. 375-378, Jun. 1999.
*Scaphoid Protocols Using the Acutrak® Bone Screw System* brochure, Toby, published by Acumed, Inc., Dec. 7, 1999.
Single Unit Osteosynthesis brochure, Surfix Technologies, Sep. 2000.
Supracondylar Cable Plate brochure, Biomet Orthopedics, Inc., 2000.
*Principle-Based Internal Fixation of Distal Humerus Fractures*, Sanchez-Sotelo et al., *Techniques in Hand & Upper Extremity Surgery*, vol. 5, No. 4, pp. 179-187, Dec. 2001.
Congruent Plate System—The Mayo Clinic Congruent Elbow Plates brochure, Acumed, Inc., May 7, 2002.
Modular Hand System brochure, Acumed, Inc., Aug. 2002.
Modular Hand System brochure, Acumed, Inc., Sep. 2002.
Periarticular Plating System brochure, Zimmer, Inc., 2002.
Jplate Diaphysis Plates for Japanese brochure, Mizuho Co., Ltd., 2002.
*An Axially Mobile Plate for Fracture Fixation*, Abel et al., *Internal Fixation in Osteoporotic Bone*, pp. 279-283, 2002.
*The Use of Interlocked 'Customised' Blade Plates in the Treatment of Metaphysical Fractures in Patients with Poor Bone Stock*, Palmer et al., *Injury, Int. J. Care Injured*, vol. 31, pp. 187-191, 2002.
3.5 mm LCP™ Proximal Humerus Plate technique guide, Synthes (USA), 2002.
Titanium Wire Plate Osteosynthesis System According to Dr. Gahr internet printout, Erothitan Titaniumplantate AG, print date Feb. 6, 2003.
Bilder internet printout, Martin GmbH & Co. KG, print date Sep. 5, 2003.
International Search Report for PCT Patent Application Serial No. PCT/US03/22904, Dec. 4, 2003.
*The Use of a Locking Custom Contoured Blade Plate for Peri-Articular Nonunions*, Harvey et al., *Injury, Int. J. Care Injured*, vol. 34, pp. 111-116, 2003.
*Salvage of Distal Tibia Metaphyseal Nonunions With the 90° Cannulated Blade Plate*, Chin et al., *Clinical Orthopaedics and Related Research*, No. 409, pp. 241-249, 2003.
Rib Securing Clamped Plate internet printout, Sanatmetal, print date Sep. 22, 2004.
Acromio-Clavicular Plates description page, author and date unknown.
ECT Internal Fracture Fixation brochure, Zimmer, Inc., undated.
ECT Internal Fracture Fixation System order information brochure, Zimmer, Inc., undated.
NexGen Osteotomy System (OS) surgical technique brochure, Zimmer, Inc., undated.
Spider™ and Mini-Spider™ Limited Wrist Fusion System brochure, Kinetics Medical Incorporated, undated.
Spider™ Limited Wrist Fusion System brochure, Kinetics Medical Incorporated, undated.
Zuelzer Hook Plates description page, Codman & Shurtleff, Inc., p. 808, undated.

*Biomechanical Evaluation of the Schuhli Nut,* Kolodziej, et al., *Clinical Orthopaedics and Related Research,* vol. 347, pp. 79-85, Feb. 1998.
Internal Fixation in Osteoporotic Bone, An, Y.H., p. 83, 2002.
*Zespol Bone Screws,* in *Mikromed—Catalogue 2004* (Nov. 2004), available at http://www.mikromed.pl/katalog/Main/main_eng.htm and http://www.mikromed.pl/katalog/zespol_eng/wkrety.htm.
*Zespol Bone Plates,* in *Mikromed—Catalogue 2004* (Nov. 2004), available at http://www.mikromed.pl/katalog/Main/main_eng.htm and http://www.mikromed.pl/katalog/zespol_eng/plytki.htm.
SmartLock Locking Screw Technology, advertisement, *The Journal of Hand Surgery,* vol. 30A, No. 1, Jan. 2005.
*Biological Plating: A New Concept to Foster Bone Healing,* Synthes (USA), 1991.
*Treatment by Plates of Anteriorly Displaced Distal Radial Fractures,* Ducloyer, *Fractures of the Distal Radius,* pp. 148-152, 1995.
*Management of Comminuted Distal Radial Fractures,* Jupiter et al., *Fractures of the Distal Radius,* pp. 167-183, 1995.
*Open Reduction of Intra-Articular Fractures of the Distal Radius,* Amadio, *Fractures of the Distal Radius,* pp. 193-202, 1995.
May Anatomical bone Plates: Plates, Bone Screws and Instruments brochure, pp. 3-4 and 10-15, Waldemar Link GmbH & Co., 1995.
Forte Distal Radial Plate System brochure, Zimmer, Inc., 1995.
*Design and Biomechanics of a Plate for the Distal Radius,* Gesensway et al., *Journal of Hand Surgery,* vol. 20, No. pp. 1021-1027, 1995 (abstract only provided).
*Fractures of the Distal Radius: A Practical Approach to Management,* Fernandez et al., pp. 103-188, 1996.
Titanium Distal Radius Instrument and Implant Set standard contents description pages, Synthes, Mar. 1997.
*Prospective Multicenter Trial of a Plate for Dorsal Fixation of Distal Radius Fractures,* Ring et al., *The Journal of Hand Surgery,* vol. 22a, No. 5, pp. 777-784, Sep. 1997.
*Treatment of Displaced Intra-Articular Fractures of the Dead End of the Radius With Plates,* Fitoussi et al., *The Journal of Bone and Joint Surgery,* vol. 79, No. 9, pp. 1303-1312, 1997 (abstract only provided).
The Titanium Distal Radius Plate, technique guide, Synthes (USA), 1997.
TriMed Wrist Fixation System brochure, TriMed, Inc., 1997.
SCS/D Distal Radius Plate System brochure, Avanta Orthopaedics, 1997.
*Intra-Articular Fractures of the Distal Aspect of the Radius,* Trumble et al., *Journal of Bone and Joint Surgery,* vol. 80A, No. 4, pp. 582-600, Apr. 1998.
*Complications of the AO/ASIF Titanium Distal Radius Plate System (π Plate) in Internal Fixation of the Distal Radius: A Brief Report,* Kambouroglou et al., *Journal of Hand Surgery,* vol. 23A, No. 4, pp. 737-741, Jul. 1998.
SCS/V Distal Radius Plate Volar brochure, Avanta Orthopaedics, 1998.
*Delayed Rupture of the Flexor Pollicis Longus Tendon After Inappropriate Placement of the π Plate on the Volar Surface of the Distal Radius,* Nunley et al., *Journal of Hand Surgery,* vol. 24, No. 6, pp. 1279-1280, Nov. 1999.
TiMAX Pe.R.I. Small Fragment Upper Exremity description pages, DePuy ACE Medical Company, 1999.
The Distal Radius Plate Instrument and Implant Set technique guide, Synthes (USA), 1999.
*Outcome Following Nonoperative Treatment of Displaced Distal Radius Fractures in Low-Demand Patients Older Than 60 Years,* Young, *Journal of Hand Surgery,* vol. 25A, No. 1, pp. 19-28, Jan. 2000.
*Comparison of Three Different Plating Techniques for the Dorsum of the Distal Radius: A Biomechanical Study,* Peine et al., *Journal of Hand Surgery,* vol. 25A, No. 1, pp. 29-33, Jan. 2000.
*Distal Radial Metaphysical Forces in an Extrinsic Grip Model: Implications for Postfracture Rehabilitation,* Putnam et al., *Journal of Hand Surgery,* vol. 25A, No. 3, pp. 469-475, May 2000.
TriMed Wrist Fixation System internet description pages, TriMed, Inc., 2001.
Titanium Distal Radius Plates description page, Synthes (USA), 2001.
Locon-T Distal Radius Plating System case study and surgical method, Wright Medical Technology, Inc., 2001.
*Open Reduction and Internal Fixation of Unstable Distal Radius Fractures: Results Using the Trimed Fixation System,* Konrath et al., *Journal of Orthopaedic Trauma,* vol. 16, No. 8, pp. 578-585, 2002.
Locon-T Distal Radius Plating System brochure, Wright Medical Technology, Inc., 2002.
*Distal Radius Fracture,* Tornetta, *Journal of Orthopaedic Trauma,* vol. 16, No. 8, pp. 608-611, 2002.
*Comparison of Different Distal Radius Dorsal and Volar Fracture Fixation Plates: A Biomechanical Study,* Osada et al., *Journal of Hand Surgery,* vol. 28A, No. 1, pp. 94-104, Jan. 2003.
*Tendon Function and Morphology Related to Material and Design of Plates For Distal Radius Fracture Fixation: Canine Forelimb Model,* Turner et al., Orthopaedic Research Society, Feb. 2003.
*Fractures of the Distal Aspect of the Radius: Changes in Treatment Over the Past Two Decades,* Simic, *Journal of Bone and Joint Surgery,* vol. 85-A, No. 3, pp. 552-564, Mar. 2003.
*Palmar Plate Fixation of AO Type C2 Fracture of Distal Radius Using a Locking Compression Plate—A Biomechanical Study in a Cadaveric Model,* Leung et al., *Journal of Hand Surgery,* vol. 28B, No. 3, pp. 263-266, Jun. 2003.
*Functional Outcome and Complications Following Two Types of Dorsal Plating for Unstable Fractures of the Distal Part of the Radius,* Rozental et al., *Journal of Bone and Joint Surgery,* vol. 85, No. 10, pp. 1956-1960, 2003 (abstract only provided).
*Fixation of Unstable Fractures of the Volar Rim of the Distal Radius with a Volar Buttress Pin®,* Hooker et al., 2003.
*Results of Palinar Plating of the Luncate Facet Combined with External Fixation for the Treatment of High-Energy Compression Fractures of the Distal Radius,* Ruch et al., *J. Orthop. Trauma,* vo. 18, No. 1, pp. 28-33, Jan. 2004.
Synthes Volar Distal Radius Locking Plate internet description page, Orthocopia, LLC, 2004.
VAL Plate description page, US Implants, undated.
Esser Complete Distal Radius Plate System, undated.
Proximal Humerus Fractures operative technique, Esser, undated.
MIfx Dorsal IM Plate, brochure, DVO Extremity Solutions, Sep. 2005.

* cited by examiner

BONE PLATES WITH SLOTS

CROSS-REFERENCES TO PRIORITY APPLICATIONS

This application is based upon and claims the benefit under 35 U.S.C § 119(e) of U.S. Provisional Patent Application Ser. No. 60/512,323, filed Oct. 17, 2003, which is incorporated herein by reference in its entirety for all purposes.

CROSS-REFERENCES TO OTHER APPLICATIONS

This application incorporates by reference in their entirety for all purposes the following U.S. patent applications: Ser. No. 10/716,719, filed Nov. 19, 2003, now U.S. Pat. No. 7,090,676; Ser. No. 10/717,401, filed Nov. 19, 2003, now U.S. Pat. No. 7,153,309; Ser. No. 10/717,402, filed Nov. 19, 2003, and Ser. No. 10/717,399, filed Nov. 19, 2003.

This application incorporates by reference in their entirety for all purposes the following U.S. provisional patent applications: Ser. No. 60/427,908, filed Nov. 19, 2002; Ser. No. 60/427,910, filed Nov. 19, 2002; Ser. No. 60/512,111, filed Oct. 17, 2003; Ser. No. 60/512,136, filed Oct. 17, 2003; and Ser. No. 60/512,322, filed Oct. 17, 2003.

This application incorporates by reference in its entirety for all purposes PCT Patent Application Serial No. PCT/US02/18623, filed Jun. 10, 2002.

FIELD OF THE INVENTION

The invention relates to plates for fixing bones. More specifically, the invention relates to bone plates having slots configured to permit positioning of the bone plates on bone, and methods of using the bone plates for bone fixation.

BACKGROUND

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bone's that become damaged should be repaired promptly and properly. Typically, a fractured or cut bone is treated using a fixation device, which reinforces the bone and keeps it aligned during healing. Fixation devices may include external fixation devices (such as casts and fixators) and/or internal fixation devices (such as bone plates, nails, and bone screws), among others.

Bone plates are sturdy internal devices, usually made of metal, that mount directly to the bone adjacent the fracture (or osteotomy). To use a bone plate to repair a discontinuity of a bone, a surgeon typically (1) selects an appropriate plate, (2) reduces the discontinuity (e.g., sets the fracture), and (3) fastens the plate to bone portions disposed on opposite sides of the discontinuity using suitable fasteners, such as screws and/or wires, so that the bone portions are fixed in position.

Despite direct access to the bone portions when applying a bone plate, the surgeon may have difficulty fixing the bone portions with the correct alignment. For example, one or more of the bone portions may be relatively small and/or displaced from the bone plate. As a specific example, in fixation of fractures of the distal radius, a distal bone fragment may be difficult to position properly. More generally, during attachment of any bone plate, fasteners may be misplaced or misdirected so that bone portions move away from a desired positioning as the fasteners are tightened. Accordingly, the relative position of bone portions may need to be adjusted as the bone plate is being secured to a bone to achieve proper reduction of a bone discontinuity.

SUMMARY OF THE INVENTION

The invention provides bone plates having slots configured to permit positioning of the bone plates on bone, and methods of using the bone plates for bone fixation.

DETAILED DESCRIPTION

The invention provides adjustable bone plates having slots configured to permit positioning of the bone plates on bone, and methods of using the bone plates to position the bone plates on bone. An adjustable bone plate, as described herein, may have an opening and a slot. Each of the opening and the slot may receive a fastener so that the fasteners cooperate with the Opening and the slot to define a permitted range Of motion of the bone plate. The permitted range may include angular (e.g., pivotal, rotational, and/or reorientational) and/or translational (e.g., center-of-mass or lateral) movement of the bone plate. In some embodiments, the adjustable bone plate may have at least a pair of slots in which the fasteners are received. The pair of slots may extend transversely to one another.

the adjustable bone plates described herein may be used in methods of positioning a bone plate on a bone after the bone plate is disposed on, and/or connected to, the bone. Such positioning may be in relation to a first bone region to which the bone plate has been connected, before the bone plate is secured to a second bone region. In some embodiments, the positioning may include translational adjustment of the bone plate after placement of the first fastener and angular adjustment after placement of the second fastener. Furthermore, in some embodiments of the methods, the bone plates may be used to adjust the alignment of first and second bone regions while connected to the bone regions on opposing sides of a bone discontinuity, such as a fracture or cut (for example, produced by an osteotomy). Accordingly, the bone plates described herein may be used to adjust reduction of a bone discontinuity by translational and/or angular movement of the bone plate.

Further aspects of the invention are described in the following sections, including (I) an exemplary adjustable bone plate, (II) an exemplary method of using an adjustable bone plate, (III) overview of adjustable bone plates, (IV) openings of adjustable bone plates, and (V) examples.

I. An Exemplary Adjustable Bone Plate

Figure 1:
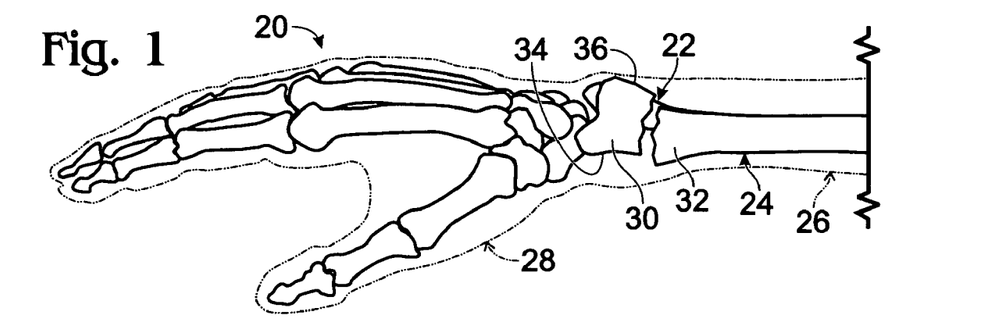
FIG. 1 is a lateral view of the bones of the right hand and distal forearm in which the radius has suffered a Colles' fracture, displacing and angulating a distal fragment of the radius dorsally.

FIG. 1 shows an upper right extremity 20 exhibiting a Colles' fracture 22, which is a very common fracture of the distal radius 24 typically caused by using an outstretched hand to break a fall. The position of the fracture is indicated relative to the skin of the distal forearm 26 and hand 28, which is shown in phantom outline in Colles' fracture 22, a smaller, distal bone fragment 30 may be displaced dorsally from a larger, proximal bone segment 32 of the radius bone. Colles' fracture 22 may be reduced, and the fractured bone fixed, with the adjustable bone plates described herein. The bone plates may be placed on the volar (anterior or lower) side 34 of the radius. This placement may reduce or avoid tendon irritation that may occur with flexion when the bone plate is attached to the dorsal (posterior or upper) side 36 of the radius. Alternatively, the bone plates described herein may be used on the dorsal surface of the distal radius or on any other suitable bone(s) or bone surface(s).

Figure 2:
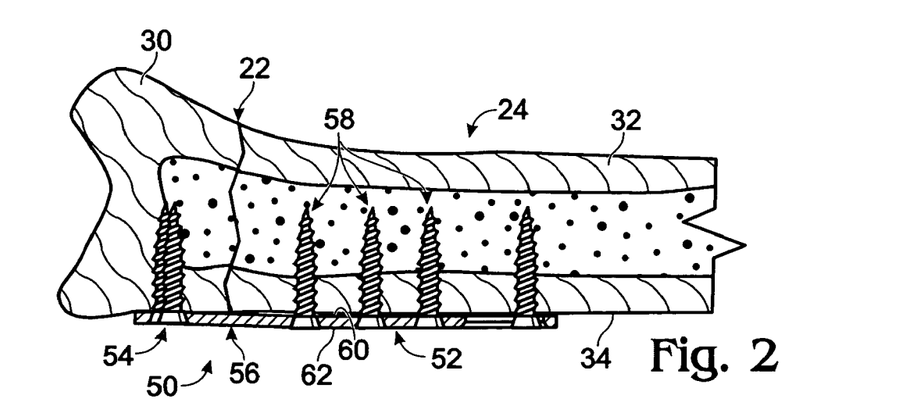
FIG. 2 is a fragmentary sectional view of the distal radius of FIG. 1, fixed with a first exemplary bone plate that is secured to the distal radius and positioned thereon using a guide slot of the bone plate, in accordance with the present teachings.

FIG. 2 shows an adjustable bone plate 50 secured to fractured distal radius 24 and positioned thereon using a guide slot of the bone plate to adjust reduction of discontinuity 22. The features and methods of use of bone plate 50 may be suitable for use with Colles' fractures, other fractures or discontinuities of the distal radius, and similar or other fractures or discontinuities of other bones or skeletal features. Bone plate 50 may include a proximal anchor portion 52 and a distal anchor portion 54 joined by a bridge region 56. Fasteners 58, such as the bone screws of the present illustration, may be used to secure proximal and distal anchor portions 52, 54 to proximal bone segment 32 and distal bone fragment 30, respectively. Bridge region 56 may be disposed adjacent discontinuity 22.

Bone plate 50 may include inner and outer surfaces 60, 62 configured to contact and oppose bone, respectively. Inner surface 60 may be disposed adjacent volar surface 34 and outer surface 62 may be spaced from the volar surface of the radius. The inner surface may be contoured to fit onto the volar surface, which may reduce the profile of the plate and/or improve its ability to contact bone, among others.

Figure 3:
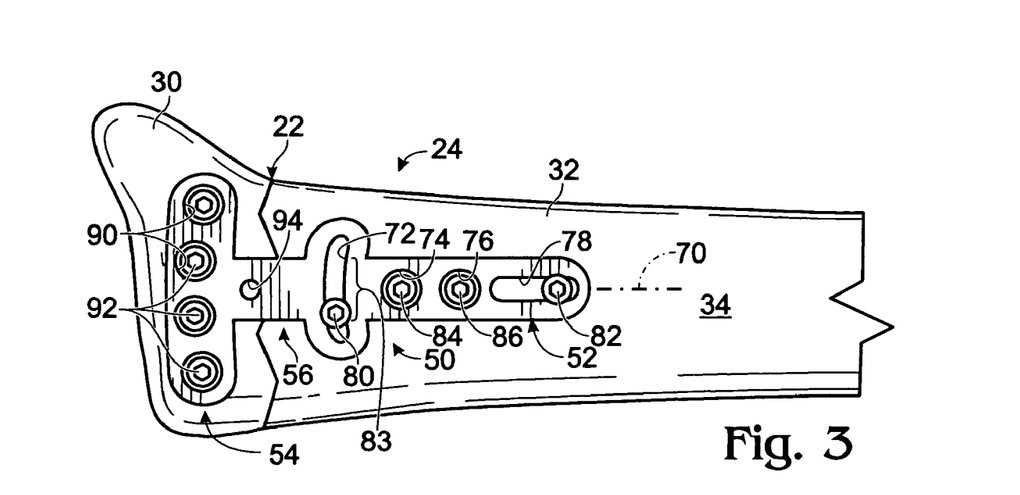
FIG. 3 is a volar view of the distal radius and the bone plate of FIG. 2.

FIG. 3 shows a plan view of bone plate 50 secured to distal radius 24 and spanning discontinuity 22. Proximal anchor portion 52 may define a central or long axis 70 of the bone plate. The bone plate may be configured so that long axis 70 is generally aligned with the long axis of the radius. However, the alignment of the axes of the plate and the bone may be adjusted during installation of the bone plate on the bone, and the final alignment of the axes need not always be parallel.

Proximal anchor portion 62 may define a plurality of openings 72-78. These openings may be defined between the inner and outer surfaces of the plate. A pair of these openings, distal and proximal openings 12 and 78, respectively, in the present illustration, may be configured to receive fasteners that cooperate with the openings to define a permitted range of motion of the bone plate relative to proximal segment 32 (and/or distal segment 30) of the radius.

One or both openings of the pair may be elongate openings, termed slots. For example, distal slot 72 may extend generally transversely to the long axis of the bone plate. Distal slot 72 may be arcuate or linear, among others. This distal slot may receive a fastener, such as bone screw 80, which may guide and restrict movement of the bone plate in cooperation with distal slot 72, so that distal 72 acts as a guide slot. Proximal slot 78 also may function to guide and/or restrict movement of the bone plate in cooperation with another fastener, such as bone screw 82, received in proximal slot 78. In some embodiments, proximal slot 78 may be configured instead as a non-elongate opening. Accordingly, bone screw 82 may define a pivot axis (or pivot axes) about which the bone plate can pivot. Bone screw 82 also or alternatively may cooperate with proximal slot 78 to guide and restrict translational movement of the bone plate relative to bone, particularly before bone screw 80 is received in distal slot 72. Proximal slot 78 is an example of a guide/pivot opening.

Slots 72, 78, may be disposed generally orthogonal to one another and on the same side or on opposing sides of bone discontinuity 22. In some embodiments, proximal slot 78 may define an orthogonal plane that intersects distal slot 72, and particularly a central portion 83 of this slot. For example, in the present illustration, proximal slot defines an orthogonal plane that bisects distal slot 72 (and the bone plate).

Additional openings 74, 76 may be configured to restrict a range of motion permitted by slots 72, 78 and their respective fasteners. Accordingly, these additional openings may be non-elongate (or elongate) and may receive fasteners, such as bone screws 84, 86, that fix the angular and/or translational disposition of the bone plate on proximal segment 32 (and/or distal fragment 30) of the distal radius.

Distal anchor portion 54 may define a plurality of openings 90 for securing this anchor portion to distal fragment 30 of the radius using distal fasteners, such as distal bone screws 92. The distal fasteners may secure the bone plate to distal fragment 30 before and/or after a translational and/or angular disposition of the bone plate on proximal segment 30 is adjusted and/or fixed.

The bone plate also may define one or more additional tool-engagement sites such as openings 94 configured to be engaged by a position-adjustment tool, such as a graspable handle, for adjusting the position of the bone plate on bone. The tool-engagement sites may be any region(s) of the bone plate configured to couple a position-adjustment tool to the bone plate. The tool-engagement site(s) may be positioned at an opposite end of the bone plate from the guide/pivot opening(s), to increase the lever or moment arm provided by the handle for adjusting the angular disposition of the plate. In these embodiments, a guide slot may be positioned between a tool-engagement site and a guide/pivot opening. In some embodiments, the guide/pivot opening and guide slot may mount adjacent a first portion of bone, with a tool-engagement site disposed adjacent a discontinuity (in a bridge region of the bone plate) and/or disposed adjacent a second portion of the bone separated from the first portion by the discontinuity.

The tool engagement site(s) may include a receiver structure (or structures) in, on, or about which a tool (or tools) can be received. The receiver structure may include an opening (such as opening 94) or any other space at which a tool can apply a positioning force, such as a torque, to the bone plate.

The opening may be a recess or hole defined by an edge of the bone plate, by an inner surface of the plate, by an outer surface of the plate, by inner and outer surfaces, and/or the like. For example, the opening may be configured to receive a position-adjustment tool that has a tip configured to fit into the opening. Alternatively, or in addition, a tool-engagement site may be defined by an anchor portion of the bone plate, for example, an opening in the anchor portion that can be engaged by a position-adjustment tool received threadedly or, nonthreadedly in the opening. The opening also may be configured to receive a fastener, such as a bone screw, for securing the bone plate to bone. The opening thus may be used alternately for positional adjustment(s) and securing, or may be configured to be used concurrently for both operations. The position-adjustment tool(s) typically will be disconnected or removed after the bone plate is positioned, and any associated openings may alternatively be left open or filled using a fastener or plug, among others. In some embodiments, the tool-engagement sites may be configured to be spaced from bone when the bone plate is secured to bone, with flanking segments of the bone plate apposed to bone, such that the site may be engaged by a grasping tool, among others, such as pliers.

The position-adjustment tool for use with a bone plate with slots may have any suitable structure and size. The tool may include an engagement region configured to engage the bone plate, and an interface region configured to interface with a person or another device (such as another tool or a machine). The engagement region may have any suitable feature(s) that permits and facilitates engagement with the bone plate. Such features may include a threaded section, serrations, opposing jaws, bumps, a dovetail configuration, etc. The engagement region may be configured so that the tool extends at least substantially in a direction normal from the outer surface of the bone plate or from a plane defined by the bone plate, when the engagement region is engaged with an engagement site of the bone plate. The interface region may be configured to be grasped by a person, and thus may be considered a handle. Accordingly, the interface region may be knurled and/or may include other surface features that facilitate engagement with a hand. The tool may have any suitable length that permits the interface region to be grasped or engaged and/or to apply a suitable torque. In some embodiments, the length may be greater than one-third, one-half, one, two, three, five, ten, or more times the distance between one Or more of the tool engagement sites and the guide/pivot opening(s). In the same and/or other embodiments, the length may be greater than one-third, one-half, one, two, three, five, ten, or more times the total length of the bone plate for which the tool is configured. In general, the length of the tool may be increased with larger and/or sturdier bone plates for which a greater positioning force (or torque) may be needed.

II. An Exemplary Method of Using an Adjustable Bone Plate

FIGS. 4-7 show a series of views of adjustable bone plate 50 being positioned on, and secured to, fractured distal radius 24 so that fracture 22 is reduced and the radius fixed.

Figure 4:
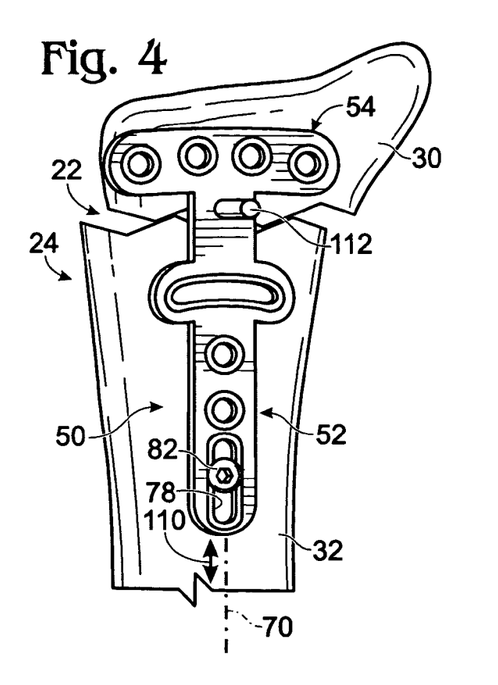
FIGS. 4-7 are a series of views of the bone plate of FIGS. 2 and 3 being positioned on, and secured to, a fractured distal radius so that its fracture is reduced and the radius fixed, in accordance with the present teachings.

FIG. 4 shows bone plate 50 positioned provisionally on the volar surface of the distal radius with the proximal and distal anchor portions 52, 54 disposed adjacent proximal segment 32 and distal fragment 30, respectively. Long axis 70 of the plate may be generally aligned With the long axis of the radius. Proximal slot 78 may have received bone screw 82 so that the shank of the bone screw has advanced partially or substantially into bone. However, the bone screw may be advanced incompletely, so that the head of the bone screw does not engage the bone plate sufficiently to restrict movement of the bone plate completely. Accordingly, the bone plate may be moved translationally, shown at 110, along a path parallel to proximal slot 78. The bone plate also may be pivoted at this stage, if desired. In some embodiments, distal fragment 30 of the radius may be connected to (and/or secured to) the bone plate at this stage so that the spacing (and/or angular disposition) of the proximal segment and distal fragment may be adjusted. The plate and associated bone portions may be moved using any suitable method, including purely manually and/or with the assistance of a suitable tool, such as a handle, among others, as described below. In the illustrated embodiment, adjustment of the plate's position, here and below, may be produced by manipulation of an optional handle 112 coupled to the bone plate. Further aspects of tools that may be suitable for adjusting the plate's positions are included in the following patent application, which is incorporated herein by reference: U.S. patent application Ser. No. 10/717,402, filed Nov. 19, 2003.

Figure 5:
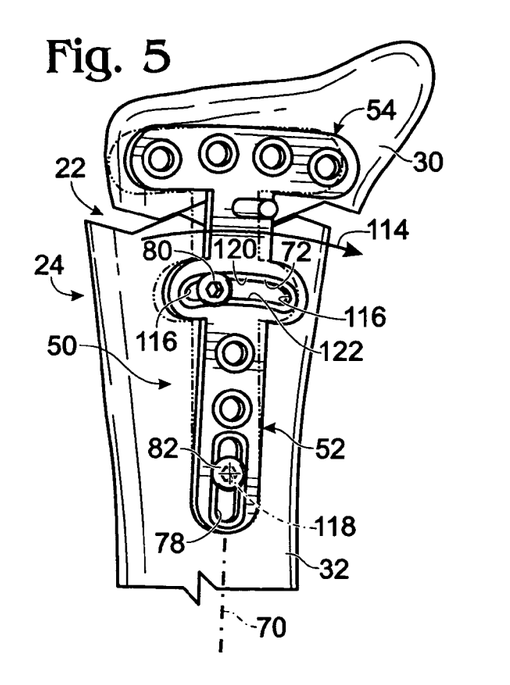

FIG. 5 shows bone plate 50 after placement of bone screw 80 (a guide screw) through distal slot 72 and into bone. Distal slot 72 may have received guide screw 80 so that the shank of the bone screw has advanced partially or substantially into bone. However, guide screw 80 may be advanced incompletely, so that the head of the bone screw does fully restrict movement of the bone plate by contact with the wall of distal slot 72. Accordingly, the angular/lateral disposition of the bone plate may be adjusted, shown at 114, relative to proximal segment 32 and/or the long axis of the radius. The range of permitted angular adjustments may be defined, at least partially, by distal slot 72 in cooperation with bone screw 80. Accordingly, contact of bone screw 80 with the lateral edges 116 of the transverse slot may stop lateral movement of the slot relative bone screw 80. In some embodiments, bone screw 82 may define a pivot axis 118 about which the plate may be pivoted. Distal slot 72 thus may have a radius of curvature at least substantially equal to the distance between bone screws 80, 82, and to a distance measured between the openings/slots in which these bone screws are received.

If bone plate 50 is pivoted, the radius of pivotal movement may be defined by the distance between pivot screw 82 and guide screw 80. Thus, this distance may change based on the position of pivot screw 82 in proximal slot 78 when guide screw 80 is placed through distal slot 72 and into bone. Accordingly, distal slot 72 may be configured to permit different pivot radii. This distal slot may have a different radius of curvature on its distal and proximal edges 120, 122, respectively. Alternatively, this transverse slot may have a width (measured parallel to long axis 70 of the plate) that is sufficiently greater than the diameter of guide screw 80 to accommodate a range of pivot radii. In some cases, the relative diameters of the head and shaft of the guide screw may be selected to enhance the ability of the guide screw to accommodate different radii, for example, by using a screw with an oversized head. In some embodiments, the bone plate may be permitted some translational movement relative to screw 82 as the angular disposition of the bone plate is adjusted, to correct for any difference between the, radius of curvature of distal slot 72 and the distance between bone screws 80, 82 (or when distal slot 72 is not curved). Accordingly, the angular disposition of the bone plate may be adjusted by movement that is nonpivotal.

Figure 6:
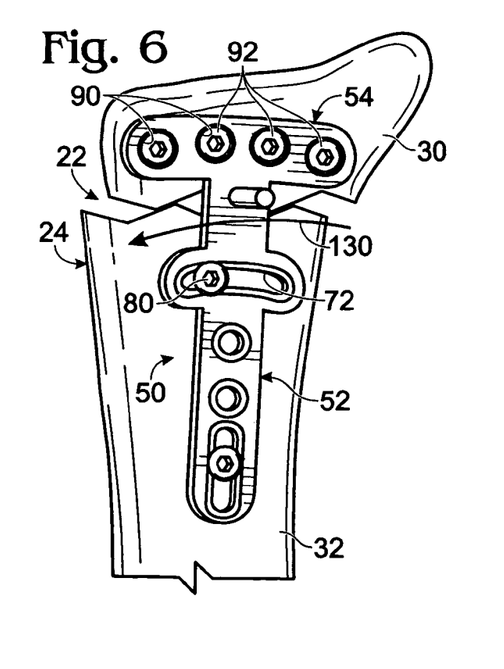

FIG. 6 shows bone plate 50 after placement of bone screws 92 into distal openings 90 to secure distal anchor portion 54 to distal fragment 30. Now, movement of distal slot 72 relative to bone screw 80, indicated at 130, may adjust the angular and lateral disposition of distal fragment 30 relative to proximal segment 32, to adjust reduction of the fracture.

Figure 7:
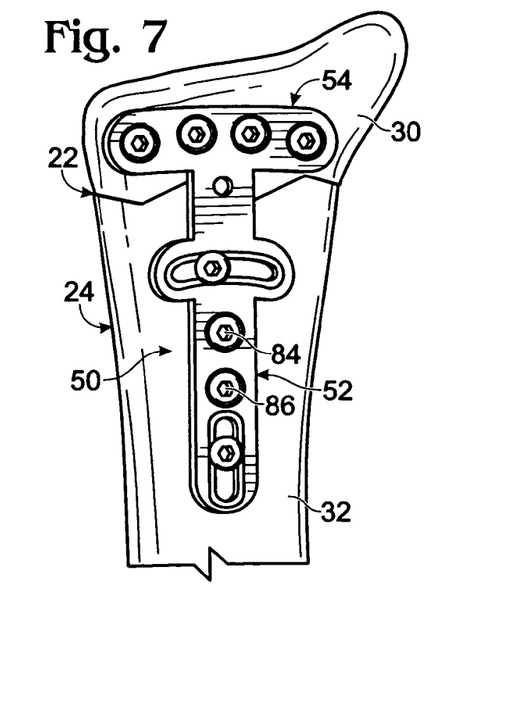

FIG. 7 shows bone plate 50 after placement of additional bone screws 84, 86 to fix the angular and/or translational disposition of the bone plate on the bone. Thus bone plate 50 is fixing the relative positions of distal fragment 30 and proximal segment 32 to which the bone plate is secured. Handle 112 (see FIG. 4) also has been uncoupled from the plate, for example, by reversing threaded engagement with the bone plate, so that soft tissue may be replaced over the bone plate and any incision closed.

III. Overview of Adjustable Bone Plates

Adjustable bone plates as described herein generally comprise any relatively low-profile (or plate-like) fixation device configured to stabilize at least one bone by attachment to the bone and including one or more slots for positioning the bone plates in situ. The fixation device may be configured to span a bone discontinuity (such as a fracture, a cut, a bone joint, etc.) so that the fixation device fixes the relative positions of bone portions disposed on opposing sides of the bone discontinuity. The fixation device generally is configured to be disposed in contact with an outer surface of the bone and thus may be positioned at least substantially exterior to the bone. The bone plate may be left in place permanently or removed after the associated bone has partially or completely healed.

The bone plates may be of a sturdy yet malleable construction. Generally, the bone plates should be stiffer and stronger than the section of bone spanned by the plates, yet flexible (e.g., springy) enough not to strain the bone significantly. Suitable materials may be biocompatible materials (such as titanium or titanium alloys, cobalt chromium, stainless steel, plastic, ceramic, etc.) and/or bioabsorbable materials (such as polygalactic acid (PGA) polylactic acid (PLA), copolymers thereof, etc.), among others.

The bone plates may be configured to reduce irritation to the bone and surrounding tissue. For example, the bone plates may be formed of a biocompatible material, as described above. In addition, the bone plates may have a low and/or feathered profile to reduce their protrusion into adjacent tissue arid rounded, burr-free surfaces to reduce the effects of such protrusion.

The bone plates may have at least one, and generally two or more, distinct anchor (or bone-attachment) portions, configured to be secured to a bone. Each anchor portion may be structured for a specific portion of a bone, generally to fit against a surface region of bone adjacent a bone discontinuity. For example, the bone plates may include a proximal anchor portion for attachment to a more proximal region of a bone, and a distal anchor portion for attachment to a more distal region of the same bone. In some embodiments; the bone plates may include a support (or buttress) portion connected to an anchor portion. The support portion may lack connective features that permit a direct connection to the bone. Such a support portion may limit movement of a bone fragment using contact between the support portion and the fragment, and may include projections or prongs to engage the fragment more effectively.

The bone plates described herein may be sized and shaped to conform to particular portions of a bone (or bones). The plates may be generally elongate, with a length L, a width W, and a thickness T. Here, length $L \geq$ width $W \geq$ thickness T. In use, the long axis of the bone plates may be aligned with the long axis of the corresponding bone or may extend obliquely or even transversely relative to the bone's long axis. The length and/or width of the bone plates may be varied according to the intended use, for example, to match the plates with a preselected region of bone(s) and/or a particular injury to the bone. For example, the plates may be generally linear for use on the shaft of a long bone or may have a nonlinear shape, such as for use near an end of a bone. In some embodiments, the plates may be generally T-shaped, including an axial portion, for attachment to a shaft portion of a bone, and a transverse portion connected to the axial portion, to provide a wider platform for attachment near an end of the bone. In some embodiments, the bone plates may be configured for use on both sides of the body, such as when the bone plates are bilaterally symmetrical. In some embodiments, the bone plates may be asymmetrical and configured for use on either the left or the right side of the body.

The bone plates described herein may be configured for use on any suitable bones of the human body and/or of another vertebrate species. Exemplary bones may include bones of the arms (radius, ulna, humerus), legs (femur, tibia, fibula, patella), hands, feet, the vertebrae, scapulas, pelvic bones, cranial bones, ribs and/or clavicles, among others. Particular examples where adjustable bone plates may be suitable include the distal radius (such as the volar surface of the distal radius) and the distal tibia.

The bone plates may include inner (bone-facing) and outer (bone-opposing) surfaces. One or both of these surfaces may be contoured generally to follow a surface of a target bone (or bones) for which the bone plates are intended, so that the bone plates maintain a low profile and fit onto the bone(s). For example, the inner surface of a plate may be generally complementary in contour to the bone surface. The outer surface may correspond in contour to the bone surface and may be complementary to the inner surface of the plate.

The thickness of the bone plates is defined by the distance between the inner and outer surfaces of the plates. The thickness of the plates may vary between plates and/or within the plates, according to the intended use. For example, thinner plates May be configured for use on smaller bones and/or on bones or bone regions where soft tissue irritation is a greater concern. Thickness may be varied within the plates. For example, the plates may become thinner as they extend over protrusions (such as processes, condyles, tuberosities, and/or the like), reducing their profile and/or rigidity, among others. The thickness of the plates also may be varied to facilitate use, for example, to make the plates thinner where they typically need to be deformed by bending and/or twisting the plates. In this way, the plates may be thicker and thus stronger in regions where they typically do not need to be contoured, such as along the shaft of the bone.

The fasteners generally comprise any mechanism for affixing a bone plate to a bone, including screws, pins, and wires, among others. A preferred fastener is a bone screw, including unicortical, bicortical, and/or cancellous bone screws. Unicortical and bicortical bone screws typically have relatively small threads for use in hard bone, such as typically found in the shaft portion of a bone, whereas cancellous bone screws typically have relatively larger threads for use in soft bone, such as typically found near the ends (periarticular regions) of a long bone. Unicortical bone screws penetrate the bone cortex once, adjacent the bone plate. Bicortical bone screws penetrate the bone cortex twice, adjacent the bone plate and opposite the bone plate. Generally, unicortical screws provide less support than bicortical screws, because they penetrate less cortex. The size and shape of the fasteners may be, selected based on the size, shape, and disposition of the openings, or vice versa. For example, unicortical bone screws may be suitable with particular arrangements of openings.

Bone plates as described herein may be attached to or otherwise associated with bone using any suitable method or procedure. For example, as mentioned above, a surgeon may (1) select an appropriate plate, (2) reduce (set) any discontinuity in the bone, and (3) fasten the plate to opposite sides of the discontinuity using suitable fasteners, such as screws and/or wires, so that portions of the bone are fixed in position. These steps may be performed manually and/or mechanically, for example, using a guide system as described in the following patent application, which is incorporated herein by reference: U.S. patent application Ser. No. 10/717,401, filed Nov. 19, 2003, now U.S. Pat. No. 7,153,309.

IV. Openings of Adjustable Bone Plates

The adjustable bone plates generally include a plurality of openings, with at least one elongate opening. The openings may be adapted to receive fasteners for connecting and/or securing the plates to bone. Alternatively, or in addition, the openings may be adapted to alter the local rigidity of the plates, to permit the plates to be manipulated with a tool (such as an attachable handle), and/or to facilitate blood flow to a fracture or surgical site to promote healing, among others.

The openings may have any suitable positions within each portion of a bone plate. The openings may be arrayed generally in a line along a portion of the plate, for example, centered across the width of an anchor portion of the plate. Alternatively, the openings may be arranged nonlinearly, for example, disposed in a curved or staggered arrangement. In some embodiments, the openings may be threaded (or nonthreaded) openings configured so that a set of bone screws, particularly unicortical bone screws, can be directed along nonparallel paths guided by threaded (or nonthreaded) engagement of the bones screws with the openings, for example, to increase the purchase of the set of bone screws on bone. Further aspects of openings that may be suitable for adjustable bone plates are described in more detail in the following patent application, which is incorporated herein by reference: U.S. Provisional Patent Application Ser. No. 60/512,111, filed Oct. 17, 2003.

The openings may have any suitable shape and structure. Exemplary shapes may include elongate openings (such as elliptical, oval, rectangular, etc.) or non-elongate openings (such as circular, square, equilateral triangular, etc). The openings may include counterbores configured, for example, to receive a head of a bone screw. The openings may be threaded, nonthreaded, or a mixture thereof.

The plates may include one or a plurality of slots. A slot is any elongate opening having a length that is greater than its width. In some embodiments, the length of the slot may be at least about one-and-one-half or twice the width of the slot. The slot may, be defined between opposing inner and outer surfaces of the plate.

The slot(s) may have any suitable shape, such as linear, arcuate, or angular, among others. The shape of the slot may be determined relative to a length by width plane of the plate (or such a plane defined by the slot), so that the shape of the slot is determined from a direction normal to this length by width plane. The slot may include a counterbore structure to receive, at least partially, a head of a bone screw. In some embodiments, the counterbore structure may be configured to exert a force generally parallel to the long axis of the slot when a bone screw is advanced against the counterbore structure, so that the slot acts as a compression slot.

The slot(s) may have any suitable location and disposition with the bone plate. The slot may be disposed near an end of the bone plate (as defined by the length of the plate) or near a more central position of the plate. The slot may be disposed on an axial portion of the bone plate, that is, a portion extending at least substantially parallel to the long axis of the plate and/or configured to be generally aligned with the long axis of a target bone. Alternatively, or in addition, the slot may be disposed on a nonaxial portion of the bone plate, such as a portion that extends obliquely and/or transversely relative to an axial portion (or the long axis) of the bone plate. The slot may extend, as defined by the long axis of the slot, at least substantially parallel, obliquely, and/or transversely to the long axis of the bone plate.

One or more reference marks may be disposed adjacent the slot(s). The reference marks may be arrayed in parallel with the slot, for example, arrayed linearly or in an arcuate arrangement. The reference marks may identify predefined positional adjustments to the bone plate. Further aspects of reference marks are included in the following patent applications, which are incorporated herein by reference: U.S. patent application Ser. No. 10/716,917, filed Nov. 19, 2003, now U.S. Pat. No. 7,090,676; and U.S. patent application Ser. No. 10/717,399, filed Nov. 19, 2003.

An adjustable bone plate may have any suitable number and relative disposition of slots. For example, the bone plate may have only one slot and at least one non-elongate opening configured to act cooperatively with the slot for positioning the bone plate in situ. Alternatively, or in addition, the bone plate may have two or more slots. The two or more slots may include at least one pair of slots configured to act cooperatively with each other and with fasteners placed in the pair of slots for positioning the bone plate in situ. The bone plate may include a single pair of such slots, or two or more pairs. Each pair of slots may be disposed in the same portion of the bone plate or on different portions of the plate, for example, in respective axial and transverse portions of the bone plate.

A pair of slots may have any suitable relative disposition. The slots of the pair may be disposed at least substantially orthogonally to one another, obliquely, or in parallel, In some embodiments, a first slot of the pair may define an orthogonal plane that intersects the second slot of the pair. The orthogonal plane extends from the long axis of the first slot in directions orthogonal to a length by width plane of the plate (or the slot). The orthogonal plane may intersect any suitable portion of the second slot, including a central portion of the second slot so that the second slot is generally centered about the orthogonal plane. The central portion of the second slot intersected may be the central one-half or the central one-fourth of the length of the second slot. In some embodiments, the first slot may be configured to permit translational adjustment of the plate's position, and the second slot may be configured to permit translational and/or rotational adjustment of the plate's position. Unless otherwise noted or understood from the context, in plates with three or more openings, and/or two or more slots, references to first, second, and third openings my be references to any openings or slots, and references to combinations (e.g., pairs or triplets) of openings and slots may be references to any combinations of openings and slots.

V. EXAMPLES

The following examples describe selected aspects and embodiments of the invention, including bone plates having transverse and/or axial slots, and methods of positioning the bone plates on bone after fasteners have been received in the slots. These examples are included for illustration and are not intended to limit or define the entire scope of the invention.

Example 1

Bone Plate with Paired Sets of Axial and Transverse Slots

Figure 8:
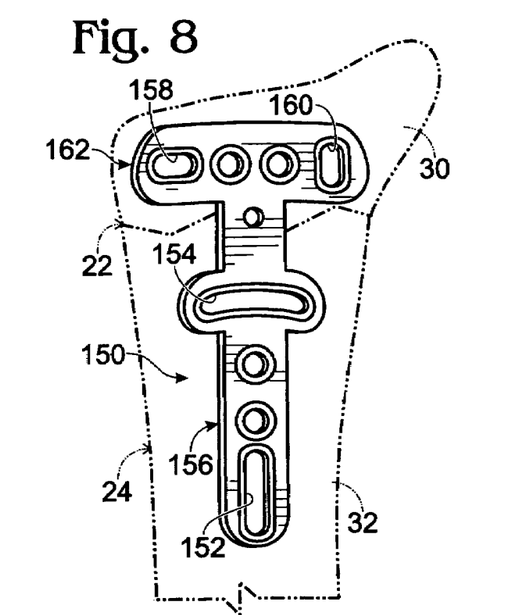
FIG. 8 is a plan view of a second exemplary bone plate having a guide slot for positioning the bone plate, in accordance with the present teachings.

This example describes an adjustable bone plate having a first pair of orthogonal slots disposed proximally (on an axial plate portion) and a second pair of orthogonal slots disposed distally (on a transverse plate portion) for positioning the bone plate relative to bone; see FIG. 8.

Bone plate 150 is shown disposed on a fractured radius 24 having a discontinuity 22. Here, and below, the fractured radius is shown in phantom outline and fasteners are omitted, to simplify the presentation. Bone plate 150 may include both an axial slot 152 and a transverse slot 154 in proximal anchor portion 156 of the, plate. These slots may be used to adjust positioning of the bone plate as described above. Bone plate 150 also may include a distal transverse slot 158 and a distal axial slot 160 in distal anchor portion 162. These slots may be used for adjusting the position of the bone plate in relation to distal bone fragment 30. Accordingly, each of slots 158, 160 may receive fasteners before either or both slots 152, 154 receive fasteners. Alternatively, each of slots 158, 160 may receive fasteners after slots 152, 154, Or these two pairs of slots may receive fasteners in an alternating order, among others.

Example 2

Bone Plate with a Transverse Slot Disposed Proximally

Figure 9:
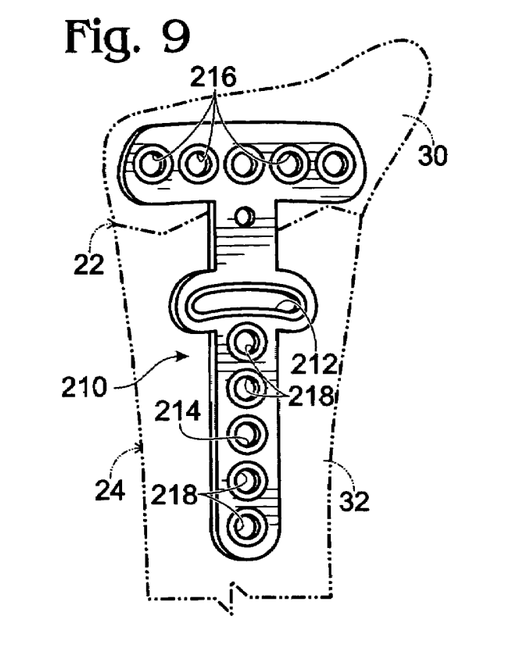
FIG. 9 is a plan view of a third exemplary bone plate having a guide slot for positioning the bone plate, in accordance with the present teachings.

This example describes an adjustable bone plate with a transverse slot disposed proximally (as part of an axial plate portion) and configured for guiding and restricting pivotal movement of the bone plate; see FIG. 9.

Bone plate 210 is shown disposed on a distal radius 24 having a discontinuity 22. In addition to transverse slot 212, the plate may include a plurality of other openings arrayed axially and/or transversely.

Plate 210 may be used to align proximal and distal pieces of the radius as follows. A pivot screw may be placed in a proximal opening 214 of the plate and advanced incompletely so that the plate can pivot about the screw. Opening 214 may be spaced from slot 212 by the radius of curvature of this slot, so that the screw in this opening defines a pivot axis. Anchor screws may be placed into the distal openings 216 of the plate, to secure distal bone piece 30 to the plate. Next, a guide screw may be placed in transverse slot 212 and into proximal segment 32 of the radius, but incompletely tightened against the plate. Pivotal movement of the plate about the pivot screw may produce pivotal/lateral movement of distal fragment 30, to adjust alignment of regions of the radius disposed on opposing sides of discontinuity 22. After a desired alignment is achieved, additional bone screws may be placed into one or more of the remaining openings 218 to fully secure the bone plate to the bone.

Example 3

Bone Plate with a Proximal Axial Slot and a Distal Transverse Slot

Figure 10:
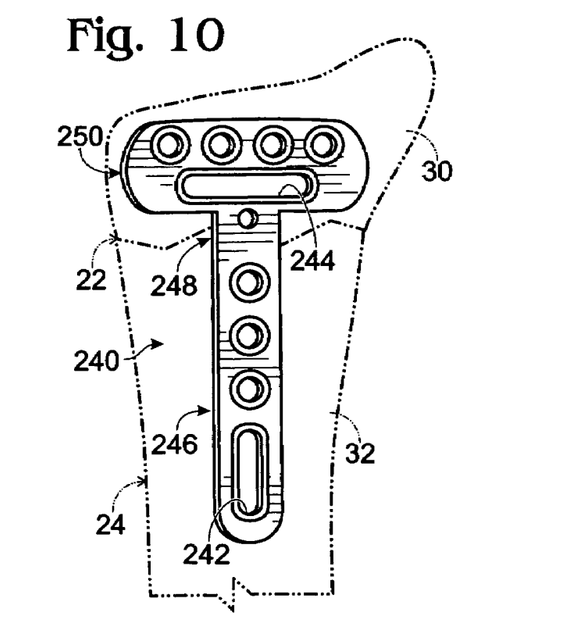
FIG. 10 is a plan view of a fourth exemplary bone plate having a guide slot for positioning the bone plate, in accordance with the present teachings.

This example describes an adjustable bone plate with orthogonal slots disposed on opposing sides of a bridge region of the plate, for adjusting the position of the bone plate on bone; see FIG. 10.

Bone plate 240 may include a pair of orthogonal slots 242, 244. Proximal slot 242 may be defined by proximal anchor portion 246 and disposed proximal to a bridge region 248 of the bone plate (and thus proximal to discontinuity 22). Distal slot 244 may be defined by distal anchor portion 250 and disposed distal to bridge region 248. Distal slot may be linear, as shown here, or arcuate, among others.

Slots 242, 244 may be utilized to position the plate on the radius as follows. A first fastener may be placed through slot 242 and advanced into proximal segment 32 of the radius. Plate 240 then may be moved translationally, parallel to slot 242, and/or pivotally, to adjust the proximal-distal and/or angular disposition of the plate. A second fastener then may be placed through distal slot 244 and into distal bone fragment 30. Alternatively, the second fastener may be placed through the bone plate and into bone before positional adjustment using proximal slot 242, so that the spacing of the proximal and distal regions of the radius can be adjusted. Next, plate 240 may be moved to adjust the angular disposition of the bone plate and the lateral disposition of distal anchor portion 250. Additional fasteners then may be placed into bone from other openings of the bone plate to fully secure the bone plate to radius 24, thereby fixing the radius.

Example 4

Bone Plate with Slots for Translational and Angular Positioning

Figure 11:
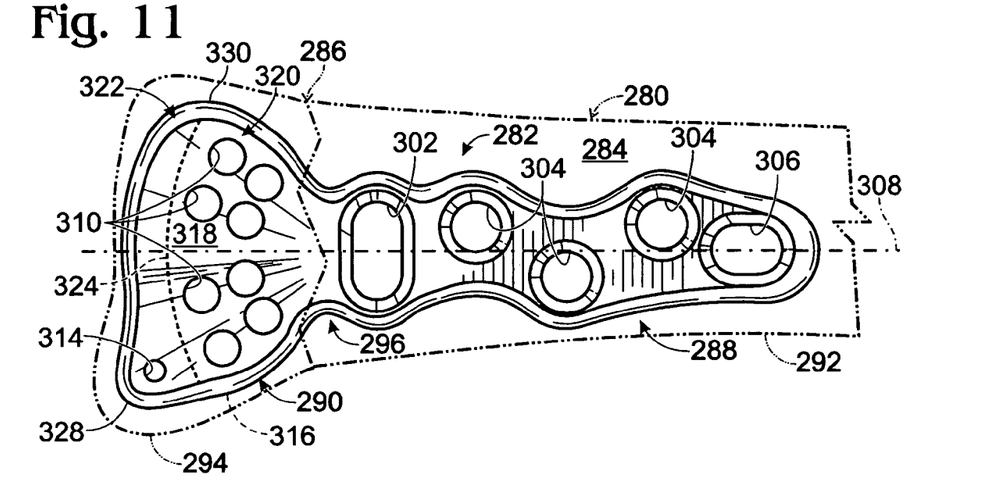
FIG. 11 is a plan view of a fifth exemplary bone plate having a guide slot for positioning the bone plate, shown apposed to a fractured bone, such as a distal radius, in accordance with the present teachings.
Figure 12:
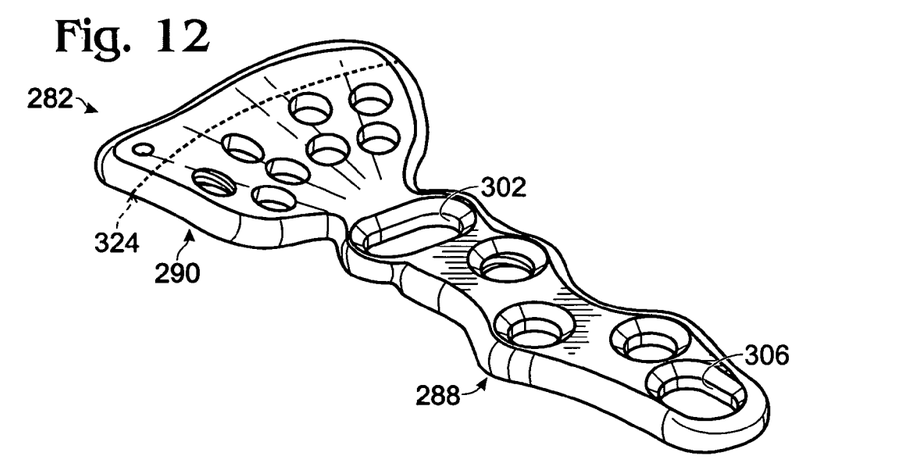
FIG. 12 is an alternative view of the bone plate of FIG. 11, shown removed from the bone.
Figure 13:
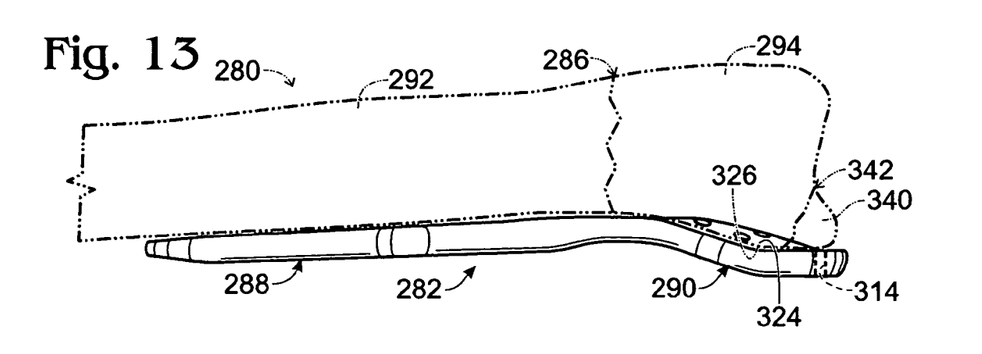
FIG. 13 is a side view of the bone plate and bone of FIG. 11.

This example describes an adjustable bone plate for fixation of a discontinuity in the distal radius, With the plate having orthogonal slots for adjusting the translational and angular dispositions of the bone plate relative to a proximal segment of the distal radius; see FIGS. 11-13.

FIGS. 11 and 12 show fractured radius 280 fixed with a fifth example of an adjustable bone plate 282. Bone plate 282 may be configured to be secured to a distal portion of the radius, such as on volar surface 284, and spanning a discontinuity in the radius, such as fracture 286 or a cut produced by an osteotomy. Bone plate 282 may be asymmetrical and configured for use on only one side of the body, on the left radius in the present illustration. Bone plate 282 may include a proximal anchor portion 288 and a distal anchor portion 290 for securing to proximal and distal bone regions 292, 294, respectively. The plate also may include a bridge region 296 connecting the anchor portions.

Proximal anchor portion 288 may be an axial portion configured to be generally aligned with the long axis of the radius. Proximal anchor portion 288 may define a plurality of openings 302-306 for receiving fasteners, such as bone screws. Openings 302, 306 may be slots disposed at least substantially orthogonal to each other. Openings 304 may be, elongate or non-elongate and may be disposed in a staggered arrangement, such as on opposing sides of a central axis 308 of the plate, to direct bone screws along staggered, nonparallel paths. Accordingly, openings 304 may define different paths of travel for bone screws based on different orientations of the walls of the openings and/or threads thereof. The perimeter of proximal anchor portion 288 may generally follow the disposition of the openings, to create a wavy or wiggly appearance to the proximal anchor portion when viewed from normal the plate.

Distal anchor portion 290 may be configured to be secured to the widened distal region of the radius. Accordingly, distal anchor portion 290 may be wider than proximal anchor portion 288 and may flare distally, to produce a fan-like shape, so that the plate overall is generally T-shaped. Distal anchor portion 290 may define a plurality of threaded and/or non-threaded openings 310 arrayed in a direction generally transverse to central axis 308 of the proximal anchor portion 288. Openings 310 may be arrayed in one or more linear or arcuate rows, among others.

Each opening 310 may be configured to receive a bone screw or other fastener (such as a pin) at a fixed angle or at a selected angle within a range of angles. The choice between a fixed or variable angle may be defined when a fastener is selected, according to how closely the screw or other fastener fits into the opening, and/or whether threaded engagement is used to fix the angle of the screw/fastener.

Distal anchor portion 290 may include one or more additional openings 314 disposed distally of openings 310. Distal opening 314 may be used, for example, to receive a fastener placed into the styloid process of the distal radius, particularly when the styloid process has been fractured.

Distal anchor portion 290 may be contoured to fit on the volar surface of the distal radius. Accordingly, distal anchor portion 290 may have an inner surface 316 that is transversely convex and an outer surface 318 that is transversely concave, particularly in a proximal section 320 of distal anchor portion 290. A distal section 322 of distal anchor portion 290 may be configured to be disposed distally of a volar-distal rim of the radius. Accordingly, distal anchor portion 290 may include a transverse contour 324, such as a depression, at the junction between proximal and distal sections 320, 322. Transverse contour 324 may be configured to receive the volar-distal rim 326 of the radius (see FIG. 13). The perimeter of distal anchor portion 290 may be shaped to correspond generally to the outline of the distal radius. For example, the distal-lateral perimeter 328 of the distal anchor portion 290 may be more angular and/or may extend farther distally than a distal-medial perimeter 330 of the plate.

FIG. 13 shows bone plate 282 disposed on the volar surface of distal radius 280. Proximal anchor portion 288 may be secured to proximal bone segment 292, and distal anchor portion 290 to distal bone fragment 294. Distal anchor portion 290 may extend over volar-distal rim 326 so that styloid process 340 may be secured to distal anchor portion 290 using a fastener placed in opening 314. Accordingly, a styloid fracture 342 may be spanned by distal anchor portion 290. The outer surface of the bone plate may be longitudinally concave, as shown here, to correspond to the contour of the volar surface of the distal radius.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A method of bone fixation, comprising:
   selecting a bone plate including a wider head portion connected to a narrower body portion, the bone plate defining a long axis and a longitudinal slot, the longitudinal slot defining a long axis that is at least substantially parallel to the long axis defined by the bone plate, the bone plate also defining a plurality of openings disposed in the head portion and further defining a transverse slot disposed generally between the longitudinal slot and the plurality of openings; and
   attaching the bone plate to at least one bone with fasteners received in the longitudinal slot, the plurality of openings, and the transverse slot,
   wherein the bone plate has opposing inner and outer surfaces, wherein an opposing surface defines a plane. wherein the long axis defined by the longitudinal slot is included in a plane that is orthogonal to the plane defined by the opposing surface and that bisects the transverse slot.

2. The method of claim 1, wherein the step of selecting a bone plate includes a step of selecting a bone plate including a transverse slot having opposing sides that each extend to opposing ends of the transverse slot, wherein the transverse slot extends along a path defined centrally between the opposing sides, and wherein an orthogonal protection of the path onto the plane defined by the opposing surface is arcuate.

3. The method of claim 1, wherein the step of selecting a bone plate includes a step of selecting a bone plate in which the plurality of openings are arrayed transversely to the long axis defined by the bone plate.

4. The method of claim 1, wherein the longitudinal slot and the transverse slot are a first pair of slots, wherein the step of selecting includes a step of selecting a bone plate in which the head portion defines a second pair of slots, and wherein the second pair of slots extend transversely to one another.

5. The method of claim 1, wherein the step of selecting includes a step of selecting a bone plate in which the transverse slot has a length and a width, and wherein the length is about twice the width.

6. The method of claim 1, wherein the step of attaching the bone plate to at least one bone includes a step of attaching the bone plate to a distal portion of a radius bone.

7. The method of claim 1, further comprising a step of selecting a bone having at least one discontinuity defining first and second portions of the bone, wherein the step of attaching includes (a) a step of placing a fastener into the first portion of the bone from the transverse slot, (b) a step of attaching the second portion of the bone to the bone plate using one or more fasteners received in one or more of the plurality of openings, (c) a step of adjusting an alignment of the first and second portions of the bone by relative movement of the bone plate and the first portion, the relative movement repositioning the fastener along the transverse slot while the bone plate is attached to the second portion of the bone, and (d) a step of fixing the alignment of the first and second portions of the bone using the bone plate after the step of adjusting.

8. The method of claim 1, further comprising a step of attaching a handle to the bone plate.

9. The method of claim 8, wherein the step of attaching a handle includes a step of disposing the handle in threaded engagement with the bone plate.

10. The method of claim 8, further comprising a step of disconnecting the handle from the bone plate.

11. A method of bone fixation, comprising:

selecting a bone plate defining a long axis and a longitudinal slot, the longitudinal slot defining a long axis that is at least substantially parallel to the long axis defined by the bone plate, the bone plate also defining a plurality of openings and further defining a transverse slot disposed generally between the longitudinal slot and the plurality of openings; and attaching the bone plate to at least one bone with fasteners received in the longitudinal slot, the plurality of openings, and the transverse slot, wherein the bone plate has opposing inner and outer surfaces, wherein an opposing surface defines a plane, wherein the long axis defined by the longitudinal slot is included in a plane that is orthogonal to the plane defined by the opposing surface and that bisects the transverse slot, wherein the transverse slot has opposing sides that each extend to opposing ends of the transverse slot, wherein the transverse slot extends along a path defined centrally between the opposing sides, and wherein an orthogonal projection of the path onto the plane defined by the opposing surface is arcuate.

12. The method of claim 11, wherein the step of selecting a bone plate includes a step of selecting a bone plate in which the plurality of openings are arrayed transversely to the long axis defined by the bone plate.

13. The method of claim 11, wherein the longitudinal slot and the transverse slot are a first pair of slots, wherein the step of selecting includes a step of selecting a bone plate defining a second pair of slots, and wherein the second pair of slots extend transversely to one another.

14. The method of claim 11, wherein the step of selecting includes a step of selecting a bone plate in which the transverse slot has a length and a width, and wherein the length is at least about twice the width.

15. The method of claim 11, wherein the step of attaching the bone plate to at least one bone includes a step of attaching the bone plate to a distal portion of a radius bone.

16. The method of claim 11, further comprising a step of selecting a bone having at least one discontinuity defining first and second portions of the bone, wherein the step of attaching includes (a) a step of placing a fastener into the first portion of the bone from the transverse slot, (b) a step of attaching the second portion of the bone to the bone plate using one or more fasteners received in one or more of the plurality of openings, (c) a step of adjusting an alignment of the first and second portions of the bone by relative movement of the bone plate and the first portion, the relative movement repositioning the fastener along the transverse slot while the bone plate is attached to the second portion of the bone, and (d) a step of fixing the alignment of the first and second portions of the bone using the bone plate after the step of adjusting.

17. The method of claim 11, further comprising a step of attaching a handle to the bone plate.

18. The method of claim 17, wherein the step of attaching a handle includes a step of disposing the handle in threaded engagement with the bone plate.

19. The method of claim 17, further comprising a step of disconnecting the handle from the bone plate.

20. A method of bone fixation, comprising:

selecting a bone plate defining a long axis, a first opening, a plurality of second openings, and a transverse slot disposed generally between the first opening and the plurality of second openings; and attaching the bone plate to at least one bone with fasteners received in the first opening, the plurality of second openings, and the transverse slot, wherein the bone plate has opposing inner and outer surfaces, wherein an opposing surface defines a plane, wherein the long axis defined by the longitudinal slot is included in a plane that is orthogonal to the plane defined by the opposing surface and that bisects the transverse slot, wherein the transverse slot has opposing sides that each extend to opposing ends of the transverse slot, wherein the transverse slot extends along a path defined centrally between the opposing sides, and wherein an orthogonal projection of the path onto the plane defined by the opposing surface is arcuate.

21. The method of claim 20, wherein the step of selecting includes a step of selecting a bone plate in which the transverse slot has a length and a width, and wherein the length is about twice the width.

22. The method of claim 20, wherein the step of attaching the bone plate to at least one bone includes a step of attaching the bone plate to a distal portion of a radius bone.

* * * * *